(12) United States Patent
Hultmark et al.

(10) Patent No.: US 11,351,313 B2
(45) Date of Patent: Jun. 7, 2022

(54) SYSTEM AND METHOD FOR MONITORING INJECTION SITE PRESSURE

(71) Applicant: The Trustees of Princeton University, Princeton, NJ (US)

(72) Inventors: Marcus Hultmark, Princeton, NJ (US); Yuyang Fan, Princeton, NJ (US); Clay Byers, Princeton, NJ (US); Matthew Fu, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 448 days.

(21) Appl. No.: 16/487,949

(22) PCT Filed: Feb. 22, 2018

(86) PCT No.: PCT/US2018/019142
§ 371 (c)(1),
(2) Date: Aug. 22, 2019

(87) PCT Pub. No.: WO2018/156707
PCT Pub. Date: Aug. 30, 2018

(65) Prior Publication Data
US 2019/0381260 A1    Dec. 19, 2019

Related U.S. Application Data

(60) Provisional application No. 62/462,422, filed on Feb. 23, 2017.

(51) Int. Cl.
*A61M 5/48* (2006.01)
*G01F 1/34* (2006.01)
(Continued)

(52) U.S. Cl.
CPC ............ *A61M 5/486* (2013.01); *A61M 5/484* (2013.01); *G01F 1/34* (2013.01); *G01F 22/02* (2013.01);
(Continued)

(58) Field of Classification Search
CPC .. A61M 2205/3334; A61M 2205/3344; A61M 5/484; A61M 5/48; A61M 2205/50;
(Continued)

(56) References Cited

U.S. PATENT DOCUMENTS 4,448,081 A    5/1984  Kolitsch et al.
5,213,573 A *  5/1993  Sorich ............... A61M 5/16859
                                                    128/DIG. 12
(Continued)

FOREIGN PATENT DOCUMENTS

CA    2300031 A1    6/2000
CN    2251548 Y     9/1997
(Continued)

OTHER PUBLICATIONS

English Translation of JP-H0755523-A (Year: 1995).*
(Continued)

*Primary Examiner* — Nilay J Shah
(74) *Attorney, Agent, or Firm* — Meagher Emanuel Laks Goldberg & Liao, LLP

(57) ABSTRACT

A system and method for monitoring the pressure of an injection site, utilizing a fluid operating in the laminar regime flowing through a calibrated tube, and measuring a pressure at one end of the calibrated tube with a pressure sensor, as well as a fluid velocity with a flow sensor, such as an elastic filament velocimeter, that comprises a nano-scale sensing element. Additional elements may be utilized, including the use of data acquisition units, processors, user interfaces, pumps, syringes, and control loops.

20 Claims, 3 Drawing Sheets

(51) Int. Cl.
*G01F 22/02* (2006.01)
*G01F 25/10* (2022.01)

(52) U.S. Cl.
CPC ..... *G01F 25/10* (2022.01); *A61M 2205/3334* (2013.01); *A61M 2205/3569* (2013.01); *A61M 2205/50* (2013.01)

(58) Field of Classification Search
CPC ....... A61M 3/0216; A61M 3/022; G01F 1/34; G01F 22/02; G01F 25/10; G01F 1/54
See application file for complete search history.

(56) References Cited

U.S. PATENT DOCUMENTS

| | | | |
|---|---|---|---|
| 5,417,106 A | | 5/1995 | Grudzien, Jr. et al. |
| 5,641,915 A | * | 6/1997 | Ortiz ........................ G01F 1/206 |
| | | | 73/861.69 |
| 5,717,146 A | * | 2/1998 | Ortiz ........................ G01F 1/206 |
| | | | 73/861.42 |
| 6,813,964 B1 | * | 11/2004 | Clark ................ A61M 5/16813 |
| | | | 73/861.52 |
| 2004/0015124 A1 | | 1/2004 | Sciulli et al. |
| 2004/0087895 A1 | * | 5/2004 | Cho .................. A61M 5/16804 |
| | | | 604/65 |
| 2004/0171983 A1 | * | 9/2004 | Sparks .................. A61M 5/365 |
| | | | 604/65 |
| 2005/0087001 A1 | * | 4/2005 | Irani ...................... G01N 11/08 |
| | | | 73/54.04 |
| 2005/0145007 A1 | * | 7/2005 | Wible ..................... G01F 25/00 |
| | | | 73/1.34 |
| 2008/0221822 A1 | * | 9/2008 | Laverdiere .......... G01F 25/0007 |
| | | | 702/100 |
| 2016/0175519 A9 | | 6/2016 | Lee et al. |

FOREIGN PATENT DOCUMENTS

| | | |
|---|---|---|
| CN | 104963845 A | 1/2015 |
| CN | 204783591 U | 11/2015 |
| JP | H0755523 A * | 3/1995 |
| JP | 2008116283 A * | 5/2008 |
| KR | 960024292 A * | 7/1996 |
| KR | 100871287 B1 * | 12/2008 |
| WO | 2009023247 A1 | 2/2009 |
| WO | 2013075109 A2 | 5/2013 |
| WO | 2016064916 A1 | 4/2016 |
| WO | 2017116499 A1 | 7/2017 |

OTHER PUBLICATIONS

English Translation of JP 2008116283 (Year: 2008).*
English translation of KR H0755523 (Year: 1995).*
Chinese Second Office Action for corresponding Application No. 2018800133067, dated Aug. 17, 2021.
International Search Report for PCT/US2018/019142, dated May 7, 2018.
Chinese First Office Action for corresponding Application No. 2018800133067, dated Jan. 27, 2021.
Supplemental European Search Report for corresponding EP Application No. 18757394, dated Jun. 29. 2020.

* cited by examiner

SYSTEM AND METHOD FOR MONITORING INJECTION SITE PRESSURE

CROSS-REFERENCE TO RELATED APPLICATIONS

This application is a national stage entry under 35 U.S.C. 371 of PCT Patent Application No. PCT/US2018/019142, filed Feb. 22, 2018. This application also claims the benefit of U.S. Provisional Application No. 62/462,422 filed Feb. 23, 2017, which is hereby incorporated in its entirety by reference.

BACKGROUND

High injection pressures have been linked to numerous medical complications, and high injection pressure has been shown to cause, for example, nerve damage and other neurological injuries. To avoid such high pressures, a variety of techniques have been used. Some physicians simply go "by feel." Others rely on implanted sensors, which adds additional trauma to the injection site. Still others use systems that rely on a mathematical model to estimate pressure. However, given the potential risks, a safer and simpler method for monitoring injection site pressure is needed and desirable.

BRIEF SUMMARY OF THE INVENTION

The disclosed system and method are drawn to safer and simpler technique for injecting patients by accurately calculating injection pressures using a pressure and a velocity sensor mounted away from the site at which the pressure is measured.

The disclosed system includes a calibrated tube, a pressure sensor, and a flow sensor, where the flow sensor has very high sensitivity to low flow rates. The velocity sensor incorporates advantageously a nano-scale sensing element and is more advantageously an elastic filament velocimeter. The system may also include pumps, syringes, processors, and injection devices. If using a processor, the processor may advantageously be configured to stop or reduce the flow of fluid if the injection pressure exceeds a predetermined threshold or rates of increase.

The disclosed method includes measuring a pressure substantially near a first end of a calibrated tube, which can include a needle, and measuring fluid velocity, preferably with an elastic filament velocimeter, at some distance from the first end, then determining a pressure at the second end based on the measured pressure and velocity. The method may also include sending a signal to control fluid flow based on the determined pressure.

The disclosed method may alternately include calibrating at least a portion of a tube having a pressure sensor substantially near a first end, and velocity sensor at some distance from that first end, penetrating a needle through a portion of tissue, causing fluid to flow past the pressure and velocity sensors, and determining pressure at an injection site based on the measured pressure and velocity and the properties of the fluid delivery system. The tube may advantageously be calibrated by applying a known pressure drop over the tube and monitoring the flowrate of a fluid with known viscosity operating in the laminar flow regime.

DETAILED DESCRIPTION

Figure 1:
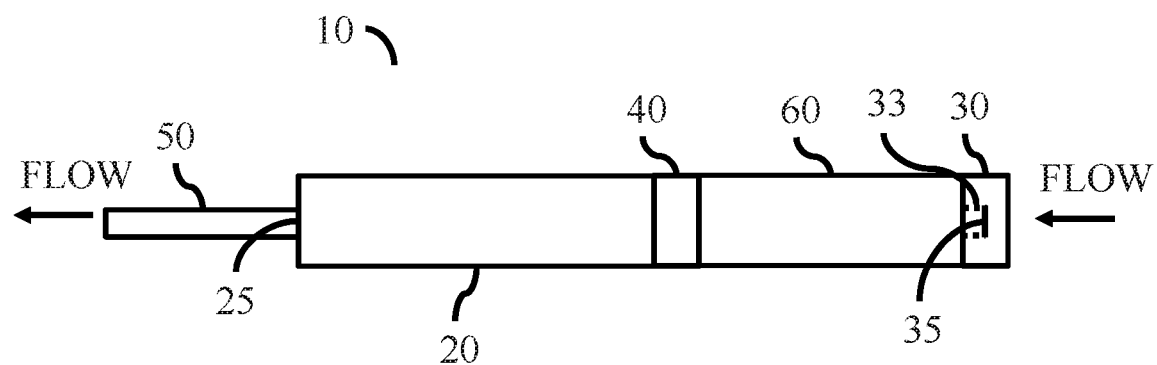
FIGS. 1-3 are depictions of example injection systems.

Reference is now made in detail to the description of the invention as illustrated in the drawings. While the invention will be described in connection with these drawings, there is no intent to limit it to the embodiment or embodiments disclosed therein.

Unless defined otherwise above, all technical and scientific terms used herein have the same meaning as commonly understood by one of ordinary skill in the art to which this invention belongs. Where a term is provided in the singular, the inventor also contemplates the plural of that term. The nomenclature used herein, and the procedures described below are those well-known and commonly employed in the art.

The singular forms "a", "an", and "the" as used herein include plural references unless the context clearly dictates otherwise.

The terms "comprise" and "comprising" as used herein is used in the inclusive, open sense, meaning that additional elements may be included.

The term "nano-scale" as used herein indicates having at least one dimension of less than 1 micrometer.

The term "tube" as used herein is intended to cover not only tubes specifically, but all similar concepts known to those skilled in the art, including but not limited to hoses, tubes, pipes, needles, and channels, whether flexible or inflexible.

As used herein, the terms "velocity" and "flowrate" are used interchangeably.

The disclosed system can be used in a variety of applications, including but not limited to various medical applications, the hydrofracturing industry, and the injection molding industry. For example, this invention may be utilized for medical research for how pressure at the injection site affects the body and the patient. By combining an elastic filament velocimeter (EFV) or similar high sensitivity sensor with a pressure sensor, and a calibrated tube set, the pressure at the injection site can be accurately estimated using, for example, laminar flow equations.

FIG. 1 depicts one embodiment of the disclosed system (10). Within the system, the velocity of a fluid flowing from a source (e.g., a syringe, a pump, etc.) is first measured by a sensor (30) advantageously containing a nano-scale sensing element. In this figure, the sensor (30) is an elastic filament velocimeter (EFV). EFVs are further described in International Application No. PCT/US2016/040975, filed Jul. 5, 2016.

The sensor (30) is typically manufactured using traditional semiconductor manufacturing techniques. One embodiment utilizes a platinum wire deposited on a silicon wafer which is then etched. The resulting device is a free-standing wire with dimensions that allows it to operate as an EFV. The freestanding sensing element can be coated with a biocompatible material. In preferred embodiments, the sensor (30) utilizes a wire filament configured to have a length longer than its width and/or thickness, and whose dimensions and properties ensure the wire can be deflected when exposed to both low and high velocity fluid streams. Preferably, the wire is less than 1 mm in length. In some embodiments, the length of the wire is between 10 and 100,000 times that of both the width and thickness. More preferably, the wire has a width greater than its thickness. In one embodiment, the nano-scale wire of the sensor is 60 μm long with cross sectional area of 2 µm by 0.1 µm. One of skill in the art will recognize that other dimensions may readily be utilized. The wire may be supported at both ends or may be free standing. The wire may also be configured to provide two sensor modes with different sensitivities in different directions. Further, the nano-scale wire may be a single, traditional, continuous filament, but it may also include but is not limited to nano-particles or nano-tubes arranged to create a conductive route, or other continuous or non-continuous arrangement that still allows an impedance to be measured across the wire.

FIG. 1 depicts one embodiment of an EFV, comprising a wire (35) positioned by prongs (33) so as to allow the flow rate of the fluid to be measured. The EFV is located at a distance from a pressure sensor (40). In FIG. 1, this distance is equal to the length of tube (60). The fluid flows past the EFV (30), through the length of tube (60), past pressure sensor (40) which detects the pressure at approximately the beginning of a calibrated tube (20).

The exact position of any sensor in the disclosed embodiments is not required, although certain locations are preferred for a given sensor. The further a sensor is located from its preferred location—such as a pressure sensor preferably positioned near the plane defining the entrance to the calibrated tube—the less accurate the system will be. Preferably, this distance between the pressure sensor and the injection site is such that the measured pressure drop in the calibrated tube is at least 10% of the full measurable range of the pressure sensor. With that in mind, one of skill in the art will typically consider an acceptable level of error that can inform the maximum acceptable distance from a preferred location. Preferably, this distance is less than 10% of the length of the calibrated tube, more preferably less than 5% of the length of the calibrated tube, and even more preferably less than 1% of the length of the calibrated tube. Thus, as used herein, the phrase "substantially near" is intended to mean a distance of less than 10% of the length of the calibrated tube.

The calibrated tube (20) may be a discrete component, although other arrangements may exist. For example, it may simply be a portion of a larger tube or piping, where the portion is configured such that it can be calibrated. The calibrated tube (20) may include an injection device such as a hypodermic needle or a catheter or it may terminate in an opening (25) that may be connected to, for example, an injection device such as a hypodermic needle or a catheter (50) through which the fluid can flow. If the calibrated tube does not include the injection device, the pressure loss in the tube should be significantly larger than the pressure drop in the injection device.

Figure 2:
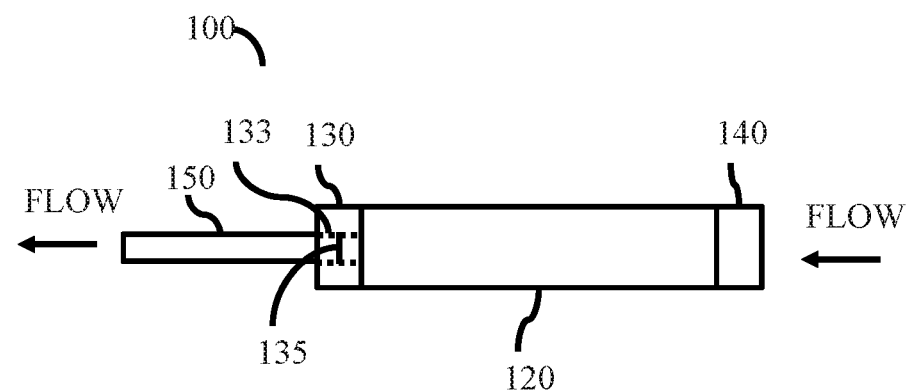

FIG. 2 depicts an alternate embodiment of the disclosed system (100). The fluid first enters the system (e.g., via a tube) into a calibrated tube (120). The pressure of the fluid entering the calibrated tube (120) is measured by a pressure sensor (140) located substantially near the entrance of the calibrated tube (120). After flowing through the calibrated tube, the velocity of the fluid is measured by an EFV (130). FIG. 2 depicts an embodiment of an EFV (130), comprising a wire (135) at least partially positioned within a channel (133) through which all of the fluid from the input tube (160) flows through. The calibrated tube is connected to an injection device such as a hypodermic needle or a catheter (150). In some embodiments, the EFV (130) and the injection device portion (150) may be a discrete component that may be removed (via unscrewing, etc.) and easily discarded and replaced. In other embodiments, the EFV (130) is separate from the injection device portion (150) and is simply positioned within the calibrated tube (120) at a defined location.

Figure 3:
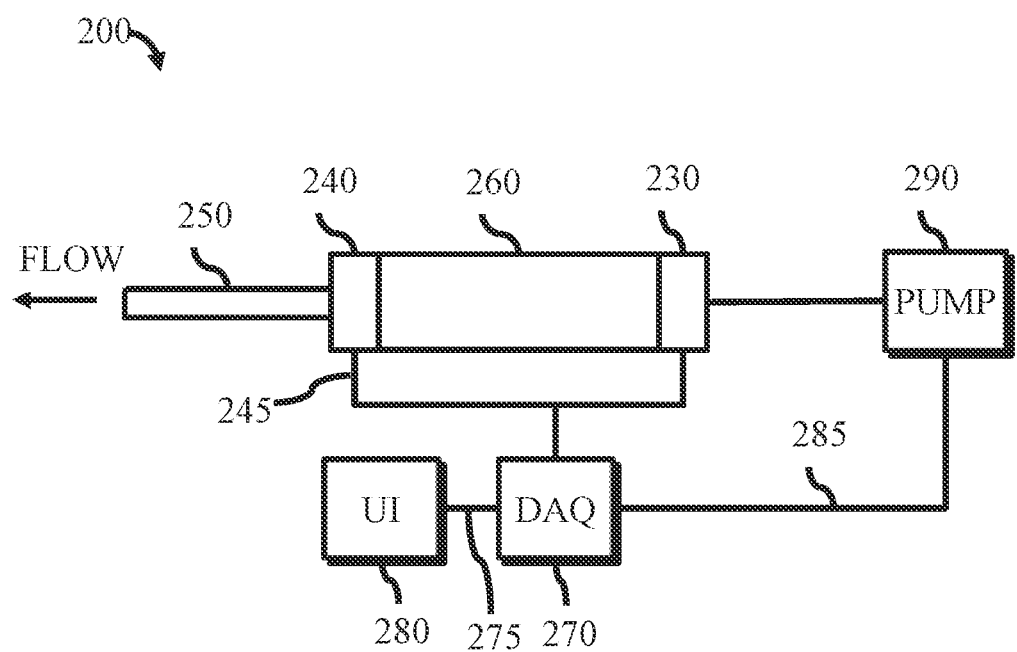

As shown in FIG. 3, the system (200) may also involve other features. For example, the EFV (230) and pressure sensor (240) may send data or signals, through wired or wireless connections (245), to a processor or data collection device (270), which may include but is not limited to a digital data acquisition (DAQ) system or a processor with a wired or wireless connection (275) to a user interface (280). Alternatively, the processor could have a wired or wireless connection (285) to a pump, syringe, or other flow control system (290) such that the flow through the calibrated tube (260) and out through the injection device (250) can be controlled. In some embodiments, to prevent possible injury to a patient, the flow may also need to be reduced or stopped if the injection site pressure exceeds some predetermined threshold or is rising too rapidly.

Figure 4:
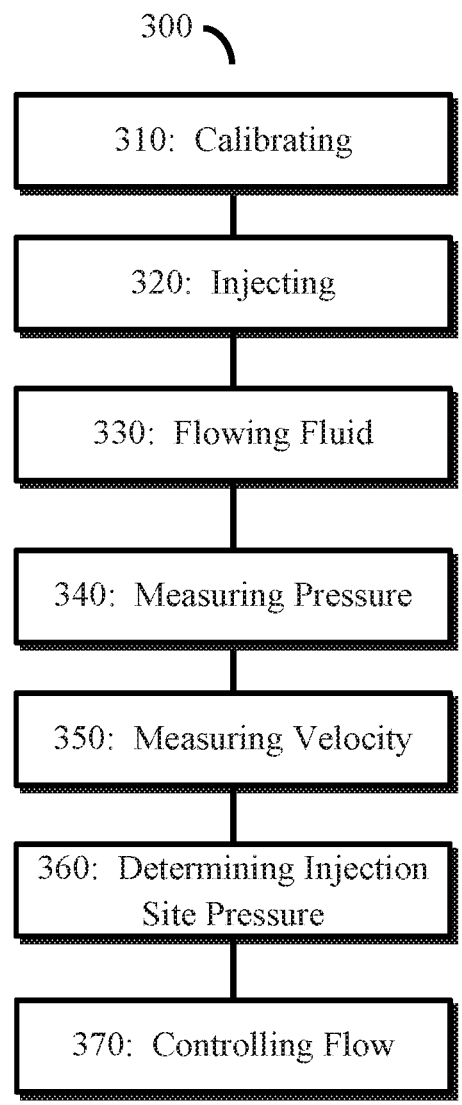
FIG. 4 is a flowchart of an embodiment of a method for determining pressure at an injection site.

FIG. 4 illustrates one method for determining pressure at an injection site. The method (300) will typically include a calibration step (310) to calibrate a tube or portion of a tube. The calibration procedure could be conducted at the time of injection or during the manufacturing of the system. A tube or portion of a tube may be calibrated by applying a known pressure drop over the tube and monitor the flowrate of a fluid with known viscosity, keeping the flow laminar. The length of the tube can then be reduced such that it confirms to a predetermined loss parameter. In embodiments using a essentially straight tube with a circular cross section, for example, Poiseuille's Law teaches that the pressure drop (delta P) over the pipe is given by $(8 \mu LQ)/(\Pi R^4)$ where L is the length of pipe, R is the radius, Q is the flowrate, and $\mu$ is the viscosity. When calibrating, the effective ratio $L/R^4$ can be determined as $(\Pi \Delta P)/(8 \mu Q)$, or equivalent for a non-circular, or non-conventional tube.

The method (300) then generally involves a setup step (320) prior to flowing fluid (330) past both the pressure sensor and the velocity sensor. In some instances, for example when tube is coupled to an injection device, such as a needle, the setup step may merely involve penetrating the needle through a portion of skin. In other instances, it may involve inserting a tube into a pre-generated hole, connector or well. In some instances, a separate setup step may not be required. For example, jet injections use a high-pressure narrow jet of the injection liquid instead of a hypodermic needle to penetrate the epidermis.

The method (300) then requires measuring both the pressure (340) and velocity or flow rate (350). Typically, the pressure is measured substantially near one end of a calibrated tube, and the fluid velocity is measured at some distance from the first end. Preferably, the velocity is measured using an elastic filament velocimeter, or other similar high sensitivity sensor. Typically, the measurements are taken simultaneously, or the time between measurements is very small (less than 1 second). However, it is envisioned that in some instances, there may be a longer delay between the measurements.

The method (300) then involves determining a pressure (360) at the second end of the calibrated tube based on the pressure and the fluid velocity. Typically, this is done using known engineering equations for viscously dominated flows. Once a calibration is complete, knowing a pressure at one location at the tube and a fluid velocity (or equivalently flow rate) allows pressure at the injection site to be calculated accurately. For example, once the fluid velocity is known, the fluid flow can be determined. Once fluid flow is known, the pressure differential can be calculated. Once the pressure differential and the pressure at the entrance of the calibrated tube are known, the pressure at the other end of the calibrated tube can be determined. If the pressure drop in the injection device is low compared to the tube it can be neglected and the pressure at the end of the tube is approximately the same as that at the injection site. If the pressure drop in the needle is not small, it should be included in the calibration procedure such that the pressure at the end of the needle can be accurately estimated.

As an example, consider a tube, including a needle, that has been calibrated by cutting it to length such that it delivers 45 ml/hour of water, in a laminar fashion, when propelled by a constant pressure pump that maintains 90 kPa gauge pressure. When a liquid with a viscosity 15 times that of water is injected through this tube, the flow sensor indicates that the flow rate is 1 ml/hour and the pressure reading at the beginning of the tube is measured to be 80 kPa. Poiseulle's law for laminar flow in a tube states that the pressure difference varies linearly with both viscosity and flow rates. Thus, the pressure drop in the described system will be ⅓ of the pressure drop in the calibration case. This implies that the pressure at the injection site at the injection site is 50 kPa above atmospheric pressure, or 30 kPa lower at the injection site compared to the pressure at the beginning of the calibrated tube.

The method may also include controlling the flow (370) through the system. Typically, this involves sending a signal to adjust the flow rate based on the determined injection site pressure. In some instances, the system may send a signal to an emergency shutoff valve to stop all flow if the pressure exceeds a particular threshold, such as a maximum pressure deemed unsafe for a given patient, or if there is a sharp increase or decrease in pressure. In other instances, a control loop may periodically adjust the flow rate up or down to keep flowrate operating near a centerline target pressure.

The method may also include providing a warning or display to a user or other individual, indicating some issue or concern with the injection system.

Various modifications and variations of the invention in addition to those shown and described herein will be apparent to those skilled in the art without departing from the scope and spirit of the invention and fall within the scope of the claims Although the invention has been described in connection with specific preferred embodiments, it should be understood that the invention as claimed should not be unduly limited to such specific embodiments.

In addition, the references listed herein are also part of the application and are incorporated by reference in their entirety as if fully set forth herein.

What is claimed:

1. A system for determining pressure at an injection site, comprising:
   a calibrated tube having a first end;
   a pressure sensor positioned substantially near the first end; and
   a flow sensor located at a distance from the pressure sensor,
   wherein at least some of fluid flowing through the calibrated tube flows past the flow sensor.

2. The system according to claim 1, wherein the flow sensor comprises a nano-scale sensing element.

3. The system according to claim 2, wherein the flow sensor is an elastic filament velocimeter or a thermal velocimeter.

4. The system according to claim 2, wherein the system further comprises at least one of a pump or syringe, configured such that the fluid flows from the pump or syringe through the nano-scale sensing element and the calibrated tube.

5. The system according to claim 1, where an injection needle is included in the calibrated tube.

6. The system according to claim 1, further comprising a processor configured to calculate the injection site pressure based on data from the pressure sensor and the flow sensor.

7. The system according to claim 6, wherein the processor is further configured to control the flow of the fluid through the calibrated tube based on the calculated injection site pressure.

8. The system according to claim 6, wherein the processor is further configured to stop the flow of the fluid if the calculated injection pressure exceeds a predetermined threshold.

9. The system according to claim 1, wherein the system further comprises a disposable injection device.

10. The system according to claim 9, wherein the disposable injection device is attached to the flow sensor.

11. A method for determining pressure at an injection site, comprising the steps of:
    providing a system according to claim 1;
    measuring a pressure substantially near the first end of the calibrated tube; measuring a fluid velocity at a distance from the first end of the calibrated tube; determining a pressure at the second end of the calibrated tube based on the pressure substantially near the first end of the calibrated tube and the fluid velocity.

12. The method according to claim 11, wherein the fluid velocity is measured with a sensor selected from the group consisting of an elastic filament velocimeter and a thermal velocimeter.

13. The method according to claim 11, where an injection needle is included in the calibrated tube.

14. The method according to claim 11, further comprising sending a signal to control fluid flow based on the determined pressure.

15. A method for determining pressure at an injection site, comprising the steps of:
    calibrating at least a portion of a tube having a first end and a second end, wherein a pressure sensor is positioned substantially near the first end, a flow sensor comprising a sensing element is positioned at a distance from the pressure sensor, and the second end is coupled to a needle;
    penetrating the needle through a portion of skin;
    causing fluid to begin flowing past the pressure sensor and the flow sensor; and
    determining the pressure at the injection site based on a pressure measured by the pressure sensor and a fluid velocity measured by the flow sensor.

16. The method according to claim 15, wherein the sensing element is a nano-scale sensing element.

17. The method according to claim 16, wherein the flow sensor is an elastic filament velocimeter or a thermal velocimeter.

18. The method according to claim 15, where the needle is included in the calibrated tube.

19. The method according to claim 15, wherein the calibration step comprises the steps of:
    applying a known pressure drop over the tube; and
    monitoring a flowrate of a calibration fluid with known viscosity, where the flowrate is in the laminar flow regime.

20. The method according to claim 15, wherein the calibration step comprises the steps of:

applying a known pressure drop over the tube; and
monitoring a flowrate of a calibration fluid with known viscosity, where the flowrate is in the laminar flow regime; and reducing a length of the tube such that the flowrate matches a predetermined value.

* * * * *